United States Patent [19]
Hamada et al.

[11] Patent Number: 5,529,779
[45] Date of Patent: Jun. 25, 1996

[54] PURIFIED PROPOLIS-EXTRACT, AND ITS PREPARATION AND USES

[75] Inventors: Shoich Hamada; Satoshi Iritani; Toshio Miyake, all of Okayama, Japan

[73] Assignee: Kabushiki Kaisha Hayashibara Seibutsu Kagaku Kenkyujo, Okayama, Japan

[21] Appl. No.: 243,548

[22] Filed: May 16, 1994

Related U.S. Application Data

[63] Continuation of Ser. No. 933,133, Aug. 20, 1992, abandoned.

[30] Foreign Application Priority Data

Aug. 27, 1991 [JP] Japan ..................... 3-296698

[51] Int. Cl.$^6$ ..................................... A61K 35/78
[52] U.S. Cl. ..................... 424/195.1; 424/539; 514/783; 514/785
[58] Field of Search ............................... 424/195.1, 539; 514/783, 785

[56] References Cited

U.S. PATENT DOCUMENTS 4,382,886  5/1983  Sosnowski ............................... 260/107

FOREIGN PATENT DOCUMENTS

| 0109993 | 6/1984 | European Pat. Off. . | |
|---|---|---|---|
| 0135601 | 4/1985 | European Pat. Off. . | |
| 61-197523 | 9/1986 | Japan ............... | A61K 35/64 |
| 1165595 | 6/1989 | Japan ............... | C07G 17/00 |
| 01165595 | 6/1989 | Japan . | |
| 9007005 | 9/1990 | Rep. of Korea . | |

OTHER PUBLICATIONS

Kuno, Kazuya, "Analysis of propolis and its quality evaluation.," Excerpt translation of *FRAGRANCE JOURNAL*, No. 83, pp. 36–39, (1987).
Donadieu, Dr. Yves, *Propolis in Natural Therapeutics*, 2nd Revised Edition, (1983).
Abstract AN 77–58998Y SU 539047 published 14 Jan. 1977.
Abstract JP63179812 published 23 Jul. 1988.
Abstract AN 87–002051 HU 850001723 published 8 May 1985.
Ellnain–Wojtaszek et al. *Herba Pol.*, 36(4), pp. 145–153, (1990). [Abstract Only].
Kandefer–Szrszen et al. *Ann Univ Mariae Curie–Sklodowska Sect C Biol*, 40(1–25), pp. 25–30, (1988) [Abstract Only].

*Primary Examiner*—Douglas W. Robinson
*Assistant Examiner*—Howard C. Lee
*Attorney, Agent, or Firm*—Browdy and Neimark

[57] ABSTRACT

Disclosed is a novel purified propolis-extract which contains the effective components of propolis in a readily absorbable- and utilizable-form in vivo, as well as having an absorbance ratio ($A_{310}/A_{660}$) of higher than 4,000, having a relatively-high quality and a satisfactory handleability, color, flavor, taste and antiseptic activity, and being substantially free of resins, waxes and dark colored impurities. The purified propolis-extract is prepared by a process comprising decreasing a readily water-soluble organic solvent in its aqueous high-concentration solution containing a crude propolis-extract to a prescribed concentration to form an upper-layer liquid containing the effective components of propolis and a lower-layer liquid containing a viscous sediment, and separating and recovering the upper-layer liquid.

9 Claims, 2 Drawing Sheets

1

PURIFIED PROPOLIS-EXTRACT, AND ITS PREPARATION AND USES

This application is a continuation of application Ser. No. 07/933,133, filed Aug. 20, 1992, now abandoned.

BACKGROUND OF THE INVENTION

1. Field of the Invention

The present invention relates to a purified propolis-extract, and its preparation and uses.

2. Description of the prior art

As described in Propolis in natural therapeutics (1983), published by Maloine Éditeur S. A., Paris, France, and *Fragrance Journal*, No. 83, pp. 20–28 and pp. 36–43 (1987), propolis is a resin-like product stored by bees in a beehive, said propolis containing resins, beeswaxes, essential oils, pollens and flavonoids, and having been used in a variety of folk medicines for a long time.

It has been known that the main activities of propolis are antiseptic activity, antioxidation activity, anti-inflammatory activity, local anesthesia activity, virus growth-inhibitory activity and immunoregulatory activity, and that the main components of propolis are flavonoids, aromatic carboxylic acids and aromatic aldehydes.

Propolis, a blackish-brown massive product, can not be readily used intact, and the main components thereof are water-insoluble- or hydrophobic-substances. Thus, propolis is generally used as a propolis extract in the form of liquid (propolis tincture) which is prepared by extracting a crude propolis specimen with a relatively-high concentration solution of a readily water-soluble organic solvent such as ethanol.

Such a propolis extract, however, has the following drawbacks when used in food products such as health foods, agents of anti-susceptive diseases such as prophylactic and therapeutic agents for susceptive-diseases, and cosmetics such as skin-refining agents and skin-whitening agents, and these render the applicability of propolis to a variety of fields difficult.

(1) The components of the propolis extract such as resins and waxes are readily crystallized. When the propolis extract is diluted with saliva, the components are readily crystallized, and this strongly inhibits the absorption and utilization of the effective components of propolis in vivo. When the propolis extract is diluted with water, the components are crystallized, and this renders the handleability very difficult.

(2) The color of the propolis extract, i.e. dark brown, is not satisfactory, and the propolis extract readily becomes opaque.

(3) The flavor and taste of the propolis extract are not satisfactory. The extract has a muddy smell and a stimulant or sharp taste.

Japanese Patent Laid-Open No. 197,523/86 proposes a method to dewax such a propolis extract with ether as an attempt to improve the above-mentioned drawbacks. The method comprises extracting a crude propolis specimen with a readily water-soluble organic solvent such as ethanol, concentrating the resultant extract, and adding to the resultant concentrate with ether to separate or remove waxes.

The method, however, has the following drawbacks: It inevitably requires a step to evaporate a readily water-soluble organic solvent, and this results in an excessive amount of energy consumption and in a complicated process, as well as accompanying a danger of fire because of the use of ether having a relatively-low flashing temperature.

As regards the effects of the method, the components of propolis such as resins and waxes are relatively-well removed, while the color, flavor and taste are still unsatisfactory.

Japanese Patent Laid-Open No. 165,595/89 proposes a method to treat propolis with an activated charcoal and/or a cation exchange resin to effect adsorption.

The method comprises extracting a crude propolis specimen with a readily water-soluble organic solvent such as ethanol, directly adding to the resultant extract with an activated charcoal and/or a cation exchange resin, and separating the effective components of propolis by filtration.

The method, however, has the following drawbacks: It requires a relatively-large amount of an activated charcoal and/or a cation exchange resin in order to satisfiably improve the color, flavor and taste of propolis, and it is not clear how to regenerate such an activated charcoal and cation exchange resin.

As regards the effects of the method, it can improve the color, flavor and taste of propolis, while the effective components of propolis are unfortunately removed by the adsorption on an activated charcoal and/or a cation exchange resin. The removal level of resins and waxes are still insufficient.

Although the combination use of the above-mentioned two methods can be considered, it only results in a much more complicated process and an increment of the production cost. Thus, the combination use is not feasible in an industrial-scale production.

It has been a great demand to establish a high-quality and purified propolis-extract containing the effective components of propolis in a readily absorbable- and utilizable-form in vivo, as well as to its industrially feasible preparation without difficulty.

SUMMARY OF THE INVENTION

The present invention was made to overcome the above drawbacks. The present inventors studied to establish a high-quality and purified propolis-extract containing the effective components of propolis in a readily absorbable- and utilizable-form in vivo, as well as having a satisfactory handleability, color, flavor and taste; and its preparation and uses; more particularly, we studied to establish a preparation of a propolis product feasible in an industrial-scale.

As a result, the present inventors found that a purified propolis-extract, which has a value of higher than 4,000 as a ratio of the absorbance at 310 nm against the absorbance at 660 nm when the absorbances are converted into those at a concentration of 2 w/w % of said propolis extract (designated as "absorbance ratio $(A_{310}/A_{660})$" hereinafter), can be favorably used, and we accomplished this invention. The present inventors also found that a high-quality and purified propolis-extract which overcomes the above drawbacks can be prepared by a process comprising decreasing the concentration of a readily water-soluble organic solvent in its aqueous high-concentration solution containing a crude propolis-extract to a prescribed concentration, forming in the aqueous solution an upper-layer liquid containing the effective components of propolis and a lower-layer liquid containing a viscous sediment, and separating and recovering the upper-layer liquid. More particularly, we found that the purified propolis-extract can be advantageously prepared by decreasing the concentration of a readily water-soluble organic solvent in its aqueous high-concentration solution to a concentration in the range of 30–55 v/v %.

The present inventors also found that a purified propolis-extract can be favorably prepared by extracting a crude propolis specimen with an aqueous low-concentration solution of a readily water-soluble organic solvent to remove impurities, extracting the resultant sediment of propolis with an aqueous solution of said organic solvent with an increased concentration of 30–55 v/v %, and recovering the resultant extract.

Furthermore, the present inventors found the following and accomplished this invention: A more highly-purified propolis-extract can be prepared by diluting such a 30–55 v/v % aqueous solution of a readily water-soluble organic solvent containing the effective components of propolis, if necessary; contacting the resultant solution with a synthetic macroporous resin to readily adsorb on it the effective components of propolis, eluting the components from the resin, and recovering the resultant components.

The present inventors also found that such a purified propolis-extract containing the effective components of propolis in a readily absorbable- and utilizable-form in vivo can be advantageously used as a composition containing thereof, for example, food products, cosmetics and agents of anti-susceptive diseases.

BRIEF DESCRIPTION OF THE ACCOMPANYING DRAWINGS

Figure 1:
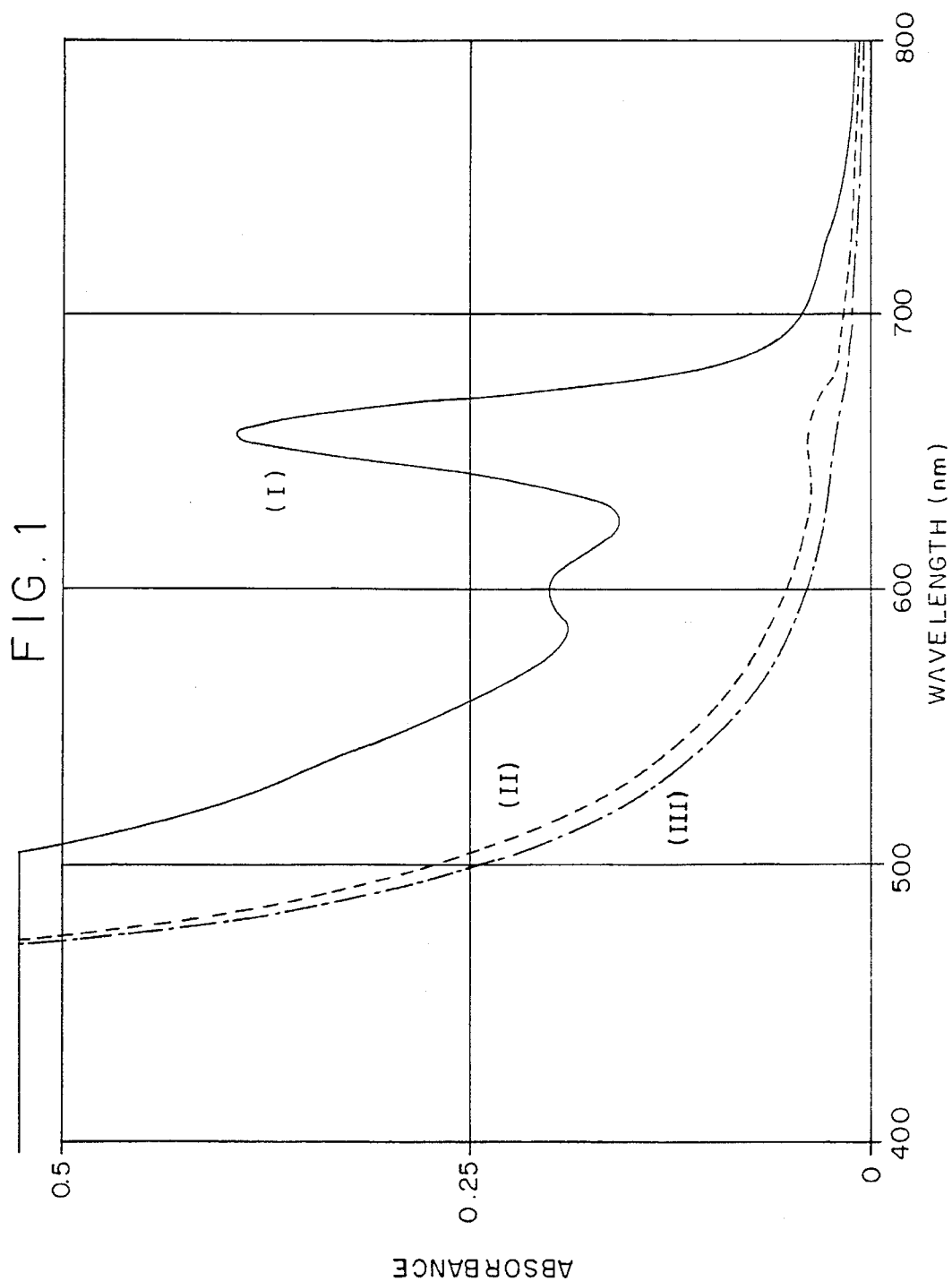
FIG. 1 shows the visual-absorption spectra of the crude propolis-extract (I) and two purified propolis-extracts (II) and (III) measured at a concentration of 2 w/w % with a 1-cm cell.
Figure 2:
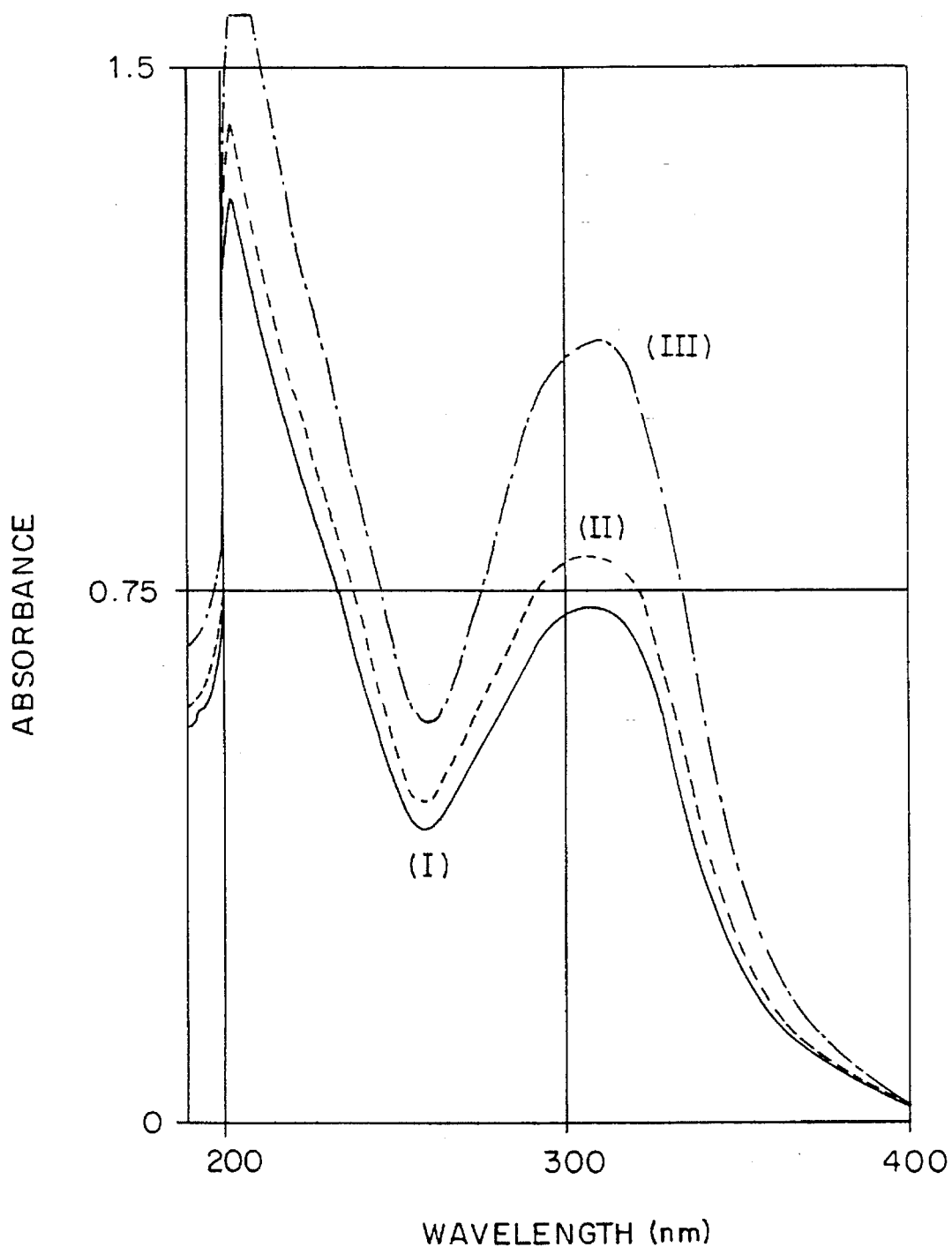
FIG. 2 shows the ultraviolet-absorption spectra of the crude propolis-extract (I) and two purified propolis-extracts (II) and (III) measured at a concentration of 0.004 w/w % with a 1-cm cell.

In FIGS. 1 and 2, the solid line means the absorption spectrum of the crude propolis-extract (I); the broken line, the purified propolis-extract (II) prepared by forming an upper-layer liquid from a crude propolis-extract and recovering the resultant upper-layer liquid; and the dotted and dashed line, the absorption spectrum of the purified propolis-extract (III) prepared by adsorbing the upper-layer liquid on a synthetic macroporous resin, eluting the substances adsorbed on the resin, and recoverying the substances.

DETAILED DESCRIPTION OF THE INVENTION

The present invention will be described in detail hereinafter.

The material propolis specimens usable in the invention are usually imported into Japan from Brazil, China, Europe and United States of America in the form of a massive product having a black, greenish black or blackish brown, and all of which can be used in the invention.

The aqueous high-concentration solutions of a readily water-soluble organic solvent containing a crude propolis-extract usable in the invention usually include crude propolis-extracts prepared by extracting a crude propolis specimen with a readily water-soluble organic solvent or its aqueous high-concentration solution of 80 v/v % or higher. Commercially available crude propolis-extracts or crude propolis-tinctures can be suitably used in the invention, if necessary.

The readily water-soluble organic solvents advantageously usable in the invention include those which can readily dissolve in water, for example, acetone, acetic acid and lower alcohols such as methanol, ethanol and isopropanol (or isopropyl alcohol). In general, an appropriate solvent is chosen to meet to its final use, and, usually ethanol is favorably used.

The aqueous high-concentration solutions of a readily water-soluble organic solvent containing a crude propolis-extract are usually those which contain a 70 v/v % or higher, preferably, 80 v/v % or higher of a readily water-soluble organic solvent together with other substances dissolved therein, for example, the effective components of propolis such as flavonoids, aromatic carbonic acids, aromatic aldehydes, and impurities derived from propolis such as resins, waxes and substances having a dark-brown color, as well as an unsatisfactory smell and taste.

It was revealed that a high-quality and purified propolis-extract is obtained by a process comprising decreasing the concentration of a readily water-soluble organic solvent in its aqueous high-concentration solution containing a crude propolis-extract to a prescribed concentration, preferably, a concentration in the range of 30–55 v/v %, in order to crystallize hydrophobic resins and waxes; allowing the resultant mixture to stand for hours, usually, at an ambient temperature for about 0.5–20 hours, in order to effect agglutination or coagulation and to form a lower-layer liquid containing a viscous sediment and an upper-layer liquid containing the effective components of propolis; and separating and recovering the upper-layer liquid.

The methods to decrease the concentration of a readily water-soluble organic solvent advantageously usable in the invention include those which contain a step of diluting a readily water-soluble organic solvent with water to a prescribed concentration.

The methods to promote the formation of upper- and lower-layer liquids usable in the invention include those which comprise decreasing the concentration of a readily water-soluble organic solvent to a prescribed concentration, and heating the resultant solution for hours at a temperature exceeding an ambient temperature, preferably, at about 40°–60° C. for about 0.1–2 hours. It was also found that the employment of the methods to decrease the concentration of a readily water-soluble organic solvent strongly improved the adsorption ability of the effective components of propolis, which were contained in an upper-layer liquid, on a synthetic macroporous resin.

Furthermore, it was found that although there was an idea to decrease the concentration of a readily water-soluble organic solvent to a much lower-level in order to better augment the above effects, the formation of a viscous sediment was inhibited at a low-concentration of about 20 v/v % or lower, and this rendered the separation or removal of the impurities difficult and the attainment of the object of the invention extremely difficult. It was also found that a high-quality and purified propolis-extract was prepared by extracting a material propolis specimen with an aqueous low-concentration solution of a readily water-soluble organic solvent having a concentration less than 20 v/v %, more preferably, a concentration of 5–15 v/v %, and extracting the resultant sediment of propolis with a 30–55 v/v % aqueous solution of a readily water-soluble organic solvent.

Accordingly, the object of the present invention is attained by a process comprising preparing a fraction containing the effective components of propolis dissolved in a 30–55 v/v % aqueous solution of a readily water-soluble organic solvent, and separating and recovering the effective components of propolis. Thus, a high-quality and purified propolis-extract, which contains the effective components of propolis, but substantially does not contain resins, waxes and other substances having a dark-brown color and a stimulant taste, can be obtained in a relatively-high yield.

Furthermore, a more purified propolis-extract can be advantageously obtained by allowing such a 30–55 v/v % aqueous solution of a readily water-soluble organic solvent containing the effective components of propolis to contact with a synthetic macroporous resin to adsorb the effective components thereon, and eluting the effective components therefrom.

The wording "synthetic macroporous resin" as referred to in the invention means non-ionic and porous synthetic-resins which have a relatively-large adsorptive area such as a styrene-divinylbenzene copolymer, phenol-formaldehyde resin, acrylic resin and methacrylate resin. Examples of such a resin are "Amberlite XAD-1", "Amberlite XAD-2", "Amberlite XAD-4", "Amberlite XAD-7", "Amberlite XAD-8", "Amberlite XAD-11" and "Amberlite XAD-12", products of Rohm & Haas Company, Philadelphia, USA; "Diaion HP-10", "Diaion HP-20", "Diaion HP-30", "Diaion HP-40" and "Diaion HP-50", products of Mitsubishi Chemical Industries Ltd., Tokyo, Japan; and "Imac Syn-42", "Imac Syn-44" and "Imac Syn-46" products of Industri de Maatshappily Activate N.V., Amsterdam, Netherlands.

In case of contacting with a synthetic macroporous resin a solution containing the effective components of propolis prepared by the above process to effect adsorption of the effective components on the resin, a method comprising preparing a 30–55 v/v % solution of a readily water-soluble organic solvent; diluting the solution with water, if necessary; and contacting the resultant solution with a synthetic macroporous resin, can be advantageously employed. Usually, a method, which contains a step of feeding a solution containing the effective components of propolis to a column packed with a synthetic macroporous resin to adsorb thereon the effective components of propolis, can be advantageously employed.

The methods to readily elute the effective components of propolis adsorbed on a synthetic macroporous resin usable in the invention include those which comprise washing a column packed with the resin by first feeding to the column water or an aqueous low-concentration solution of a readily water-soluble organic solvent, if necessary, and then feeding to the column a readily water-soluble organic solvent or a 70 v/v % or higher, preferably, 80 v/v % or higher of an aqueous solution of a readily water-soluble organic solvent.

A more purified propolis-extract can be obtained by recovering from the column a fraction containing a substance exhibiting a strong absorption-spectrum near 290–320 nm.

The elution step simultaneously regenerates a synthetic macroporous resin and enables its repeated use.

The present purified propolis-extract thus obtained is a relatively-high quality propolis-extract having an absorbance ratio ($A_{310}/A_{660}$) of higher than 4,000, and the above-mentioned effluent, extract or upper-layer liquid usually contains the effective components of propolis in an amount of about 1–25 w/w %, based on the weight of the dry solid basis (d.s.b.), as well as having a satisfactory color, flavor and antiseptic activity, and, if necessary such an effluent, extract or upper-layer liquid can be advantageously concentrated and pulverized into a purified propolis-extract powder. If necessary, such a concentrated solution can be advantageously mixed with an anhydrous saccharide or cyclodextrin to effect dehydration, followed by pulverizing the resultant dehydrated product.

The present purified propolis-extract can be used alone because it contains the effective components of propolis in a readily absorbable- and utilizable-form in vivo, and, if necessary it can be advantageously used in combination with other substances, for example, an antioxidant, stabilizer, taste-imparting agent, color-imparting agent, flavor-imparting agent and filler. More particularly, the combination use of the present purified propolis-extract with other substances, for example, vitamins such as tocopherol, carotenoid, L-ascorbic acid, α-glucosyl L-ascorbic acid, rutin and α-glycosyl rutin; organic acids such as citric acid and malic acid; and saccharides such as glucose, maltose, lactose and maltitol, can advantageously augment the activity and effect of the present purified propolis-extract, improve the stability and facilitate the handleability.

Since the present purified propolis-extract has the inherent activity of the effective components of propolis, it can be advantageously used in combination with other materials in a variety of compositions such as food products, cosmetics and agents of anti-susceptive diseases as an antiseptic agent, antioxidation agent, anti-inflammatory agent, local anesthesia activity, virus growth-inhibitory activity, immunoregulatory activity, agent of anti-hyperlipemia, ultraviolet-absorbing agent, yellow color-imparting agent, vitamin P-enriched agent, quality-improving agent and flavor-imparting agent. Thus, the present purified propolis-extract exerts an activity in the maintenance and promotion of health, the prevention and treatment of diseases, the promotion of the recovery of health from diseases, and the maintenance and improvement of skin conditions.

The purified propolis-extract can be advantageously used as an additive for urine in urine-therapy which has prevailed recently, and used as a deodorant for urine and an agent for augmenting the effect of urine-therapy.

The present purified propolis-extract has a satisfactory color, flavor and taste, as well as having a strong antiseptic activity and antioxidation activity, and well harmonizes with other substances having a saltiness, astringency, bitterness or deliciousness, and these render the extract advantageously useful as a flavor-stabilizing agent, shelf-life-improving agent and quality-improving agent in a specific health-food, as well as in a variety of general food products, for example, seasonings, Japanese-style confectoneries, Western-style confectioneries, sherbets, ice creams, beverages, spreads, pastes, pickled products, bottled and canned products, processed meat and fish meat products, processed marine products, processed milk and egg products, processed vegetable products, processed fruit products and processed cereal products.

The purified propolis-extract can be favorably incorporated into feeds and pet foods for animals, such as domestic animals, poultry, bees, silkworms and fishes, an antiseptic agent, agent to control intestinal disorder, vitamin P-enriched agent, agent for stress relief, and agent to improve taste preference.

The purified propolis-extract can be advantageously used in tobaccos, cigarettes, cosmetics and pharmaceuticals in the form of solid, paste and liquid, for example, troche, complexed vitamin, sublingual tablet, refrigerant, cachou, gargle, intubation nutrition, crude drug, internal medicine, injection, dentifrice, lip stick, lip cream, sunscreening agent, bath salts, agent of anti-susceptive diseases, skin-refining agent, skin-whitening agent and hair restorer.

The wording "agent of anti-susceptive diseases" as referred to in the invention means those which can be used in the prevention and/or treatment of susceptive diseases, and the wording "susceptive diseases" as referred to in the invention means those which can be prevented and/or treated with the present purified propolis-extract. Examples of such susceptive diseases are viral diseases, bacterial diseases, traumatic diseases, immunopathies, rheumatisms, diabetes, diseases of circulatory organs, malignant tumors and nervous diseases.

The form of such an agent of anti-susceptive diseases can be freely chosen to meet to its final use. Examples of such a form are liquid agents such as nebula, collyrium, collunarium, gargle and injection; paste agents such as ointment, cataplasm and cream; and solid agents such as powder, granule, capsule and tablet.

The dose of such an agent of anti-susceptive diseases can be adequately controlled depending on the content of the present purified propolis-extract in the agent and its administration route and frequency. Usually, a dose in the range of about 0.0001–10 g/day/adult of purified propolis-extract, d.s.b., is favorably used.

In case of cosmetics and orally administrable food products, the purified propolis-extract can be used similarly as in the case of the above agent.

The purified propolis-extract can be advantageously incorporated into a product before completion of the processing by using conventional methods, for example, mixing, kneading, dissolving, soaking, penetrating, dispersing, applying, spraying and injecting.

The following Experiments will describe the present invention in detail.

EXPERIMENT 1

Study of the Conditions for Preparing Purified Propolis-extract from Aqueous High-concentration Solution of Readily Water-soluble Organic Solvent Containing Crude Propolis-extract

EXPERIMENT 1-1

Influence of the Concentration of Readily Water-soluble Organic Solvent in Its Aqueous High-concentration Solution Containing Crude Propolis-extract on the Formation of Upper- and Lower-layer Liquids A crude propolis specimen was in an usual manner extracted with 95 v/v % aqueous ethanol solution, and the resultant sediment was washed with a small amount of water. The resultant solutions thus obtained were pooled to obtain an 80 v/v % aqueous ethanol solution containing a dark-brown crude propolis-extract (20 w/w %, d.s.b.) which was used in this experiment as a material solution.

A prescribed amount of the material solution was placed in a beaker and added with water to decrease the concentration of ethanol to 70, 60, 55, 50, 40, 30 or 20 v/v %, and the resultant solution was successively allowed to stand at 50° C. for 30 minutes and at an ambient temperature for 3 hours to observe or test the following items:

(a) The formation of an upper-layer liquid containing the effective components of propolis and a lower-layer liquid containing a viscous sediment such as resins and waxes was observed;

(b) The color of an upper-layer liquid was observed;

(c) The flavor and taste of an upper-layer liquid were tested by 12 panelists; and (d) In order to determine the amount of a solid product or a viscous sediment which was formed and removed in a lower-layer liquid, the removal percentage (%) into a lower-layer liquid was determined by the following equation I and used as a criterion to evaluate the purification effect and the difficulty of the preparation of a crude propolis-extract:

Equation I:

Removal percentage (%) into lower-layer liquid=

$$\frac{A-B}{A} \times 100$$

Note: The symbol "A" means the amount of solid substances in the material solution; and the symbol "B", the amount of solid substances in an upper-layer liquid.

The results were as shown in Table 1.

EXPERIMENT 1-2

Influence of the Purification Degree of Purified Propolis Extract on Absorbance Ratio and Antiseptic Activity The absorbance ratio ($A_{310}/A_{660}$) of an upper-layer liquid having a different concentration, prepared by the method in Experiment 1-1, as a material solution, was determined by:

(e) By using a 1-cm cell, the absorbance at 660 nm of the material solution having a concentration of 2 w/w %, and the absorbance at 310 nm of the material solution having a concentration of 0.004 w/w % was measured. The absorbance at 310 nm was multiplied by 500 to convert it into the absorbance at a concentration of 2 w/w %, and the absorbance ratio of $A_{310}/A_{660}$ was calculated.

(f) The antiseptic activity of the material solution was evaluated based on the minimum growth-inhibitory concentration (μg/ml) by using conventional agar plate dilution method wherein microorganisms of the species *Bacillus cereus* IFO 3466 and *Enterobacter aerogenes* IFO 3321 were used. The results were as shown in Table 1.

EXPERIMENT 1-3

Influence of Readily Water-soluble Organic Solvent on Absorption Ability of Effective Components of Propolis on Synthetic Macroporous Resin The strength of the absorption ability of the effective components of propolis on a synthetic macroporous resin was determined by:

(g) Each upper-layer liquid formed in each aqueous ethanol solution having a different ethanol concentration, prepared by the method in Experiment 1-1, was fed as a material solution to a column packed with "HP-20", a synthetic macroporous resin commercialized by Mitsubishi Chemical Industries Ltd., Tokyo, Japan, in an amount equal to about half volume of the resin, and fed with an aqueous ethanol solution having the same ethanol concentration of the upper-layer liquid, followed by determining the strength of the absorption ability of the effective components of propolis on the resin based on the difference between the amount of the solid substances in the material solution and that in the effluent.

The results were as shown in Table 1.

TABLE 1

| Concentration of readily water-soluble organic solvent (v/v %) | (a) | (b) | (c) | (d) | (e) | (g) | (f) A | (f) B | Judgement |
|---|---|---|---|---|---|---|---|---|---|
| 80 | Unformed | Dark brown | Muddy smell Stimulant taste | 0 | 983 | Substantially not adsorbed | 62.5 | 62.5 | Control |
| 70 | Unformed | Dark brown | Muddy smell Stimulant taste | 0 | 985 | Substantially not adsorbed | 62.5 | 62.5 | Control |
| 60 | Formed | Brown | Faint muddy smell Slight stimulant taste | 22 | 1,543 | Slight adsorption | 62.5 | 62.5 | Control |
| 55 | Formed | Orange | Satisfactory flavor and taste | 46 | 4,052 | Slight adsorption | 31.3 | 31.3 | Present invention |
| 50 | Formed | Orange | Satisfactory flavor and taste | 51 | 10,786 | Slight adsorption | 31.3 | 15.7 | Present Invention |
| 40 | Formed | Faint orange | Satisfactory flavor and taste | 64 | 8,640 | Strong adsorption | 31.3 | 15.7 | Present invention |
| 30 | Formed | Yellow | Satisfactory flavor and taste | 60 | 4,820 | Strong adsorption | 31.3 | 31.3 | Present invention |
| 20 | Formed | Milk yellow | Faint muddy smell Slight astringency | 29 | 1,926 | Strong adsorption | 62.5 | 62.5 | Control |

Note 1):
The sample having a concentration of 80 v/v % ethanol, a readily water-soluble organic solvent, is the material solution used in this experiment.
Note 2):
The expression as indicated in the column (c) is a summary of the expressions of 10 or more of 12 panelists.
Note 3):
The symbol "(a)" means the formation of upper- and lower-layer liquids; the symbol "(b)", the color of an upper-layer liquid; the symbol "(c)", the flavor and taste of an upper-layer liquid; the symbol "(d)", the removal percentage (%) into a lower-layer liquid; the symbol "(e)", absorbance ratio ($A_{310}/A_{660}$); the symbol "(f)", minimum growth-inhibitory concentration (μg/ml); and the symbol "(g)", the strength of the adsorption ability of the effective components of propolis on the synthetic macroporous resin.
Note 4):
The symbols "A" and "B" respectively mean microorganisms of the species *Bacillus cereus* and *Enterobacter aerogenes*.

As evident from the results in Table 1, the formation of upper- and lower-layer liquids was observed when the concentration of a readily water-soluble organic solvent decreased to 60 v/v % or lower. The color, flavor and taste of an upper-layer liquid containing the effective components of propolis were much more superior when the concentration of a readily water-soluble organic solvent was decreased to a concentration in the range of 30–55 v/v %, and these results well corresponded to the results in the removal percentage (%) of a viscous sediment containing impurities such as resins and waxes into a lower-layer liquid.

It was found that the highest removal percentage (%) was observed when the concentration of a readily water-soluble organic solvent was in the range of 30–55 v/v %. In contrast with this, it was found that the removal percentage (%) lowered when the concentration decreased to a low-concentration of 20 v/v %, and this rendered the purification of a propolis extract difficult.

It was also found that the absorbance ratio ($A_{310}/A_{660}$) well corresponded to the purification degree of a propolis extract, i.e. a propolis extract having an absorbance ratio exceeding 4,000 had a satisfiable color, flavor, taste and antiseptic activity, more particularly, a propolis extract having an absorbance ratio exceeding 8,000 was much more superior.

Furthermore, it was found that the adsorption ability of the effective components of propolis on a synthetic macroporous resin was high when the concentration of a readily water-soluble organic solvent was 40 v/v % or lower, while the absorption ability was low at a concentration of about 50–60 v/v % and substantially was not observed at a concentration of 70 v/v % or higher.

Accordingly, an upper-layer liquid containing the effective components of propolis and having a concentration of 30–40 v/v % of a readily water-soluble organic solvent can be directly allowed to contact with a synthetic macroporous resin to adsorb thereon the effective components of propolis. In case of an upper-layer liquid containing the effective components of propolis and having a concentration of about 50–55 v/v % of a readily water-soluble organic solvent, the liquid is, usually, suitably separated and diluted with about 0.5–2-fold volumes of water, and the resultant solution is allowed to contact with a synthetic macroporous resin.

In case of eluting the effective components of propolis adsorbed on such a synthetic macroporous resin, it is preferable to increase the concentration of a readily water-soluble organic solvent to the possible highest level, i.e. the elution step is generally effected by using a readily water-soluble organic solvent having a concentration of 80 v/v % or higher.

EXPERIMENT 2

Visible- and Ultraviolet-absorption Spectra of Crude Propolis-extract and Two Types of Purified Propolis-extracts A crude propolis-extract (specimen I) prepared by the method in Experiment 1-1; a purified propolis-extract (specimen II) prepared from an upper-layer liquid formed by decreasing the ethanol concentration of the crude propolis specimen I to 50 v/v %; and a purified propolis-extract (specimen III) prepared by the method in Experiment 1-1 in a manner that decreasing the ethanol concentration in its aqueous solution containing a crude propolis-extract to 50 v/v % to form an upper-layer liquid, separating the upper-layer liquid, diluting the resultant upper-layer liquid with equal volume of water, and allowing the resultant solution to contact with a synthetic macroporous resin, were studied on their visual- and ultraviolet-absorption spectra.

The specimens I, II and III were adjusted to give a concentration of 2 w/w % which were then subjected to measurement of their visual-absorption spectra with a 1-cm cell. The results were as shown in FIG. 1.

The specimens I, II and III were adjusted to give a concentration of 0.004 w/w % which were then subjected to measurement of their ultraviolet-absorption spectra with a 1-cm cell. The results were as shown in FIG. 2.

In FIGS. 1 and 2, the solid line means the absorption spectrum of the specimen I; the broken line, the absorption spectrum of the specimen II: and the dotted and dashed line, the absorption spectrum of specimen III.

As evident from FIG. 1, the absorption levels of the visual-absorption spectra of the specimens I, II and III decrease in this order as the purity of the effective components of propolis in the specimens increases in this order, and the peak level near at 650–660 nm corresponding to a dark-brown color strongly decreases.

As evident from FIG. 2, the absorption levels of the ultraviolet-absorption spectra of the specimens I, II and III near at 290–320 nm particularly increase in this order, and the contents of the effective components of propolis in the specimens also increase as the purity of the effective components of propolis in the specimens increases.

EXPERIMENT 3

Acute Toxicity Test

A freeze-dried specimen of a purified propolis-extract, which had been obtained from an upper-layer liquid formed by decreasing the concentration of a readily water-soluble organic solvent to 50 v/v % prepared by the method in Experiment 1-1, was tested for the acute toxicity by using 7-week-old dd mice. No mouse died up to a dose of 2.5 g. Thus, the toxicity of the specimen was extremely low.

Another freeze-dried specimen of a purified propolis-extract was prepared and tested on its acute toxicity to obtain the same result similarly as above, said purified propolis-extract being obtained similarly as in Experiment 1-1 by decreasing the concentration of a readily water-soluble organic solvent in its aqueous solution containing a crude propolis-extract to 50 v/v % to form an upper-layer liquid, diluting the resultant solution with equal amount of water, allowing the effective components of propolis in the diluted solution to adsorb on a synthetic macroporous resin, and eluting from the resin the effective components adsorbed thereon. Thus, it was revealed that the toxicity of the specimen was also extremely low.

The following Examples A and B will explain the present purified propolis-extract and compositions containing thereof as an effective component.

EXAMPLE A-1

A crude propolis specimen was in an usual manner extracted with 95 v/v % aqueous ethanol solution, and the resultant sediment was washed with a small amount of water. The resultant solutions were pooled to obtain an 80 v/v % aqueous ethanol solution containing a crude propolis-extract (about 20 w/w %, d.s.b.) was added with water to decrease the ethanol concentration to 50 v/v %, and allowed to stand at 50° C. for one hour to form an upper-layer liquid containing the effective components of propolis and a lower-layer liquid containing a viscous sediment. The upper- and lower-layer liquids were allowed to stand overnight at an ambient temperature, and the upper-layer liquid was separated to obtain a purified propolis-extract in the form of liquid having an absorbance ratio ($A_{310}/A_{660}$) of 11,015 and having a satisfactory color, flavor, taste and antiseptic activity in a yield of about 48% against the weight of the material solution containing a crude propolis-extract, d.s.b.

The product can be advantageously used intact as an antiseptic, antioxidant, anti-inflammatory agent and immunoactivator, and used in combination with other appropriate materials in food products, cosmetics and agents of anti-susceptive diseases.

EXAMPLE A-2

A crude propolis specimen was in an usual manner extracted with 90 v/v % aqueous ethanol solution, and the resultant sediment was washed with a small amount of water. The resultant solutions were pooled to obtain a 75 v/v % aqueous ethanol solution containing a crude propolis-extract (about 18 w/w %, d.s.b.) was added with water to decrease the ethanol concentration to 40 v/v %, allowed to stand at 60° C. for 20 minutes to form an upper-layer liquid containing the effective components of propolis and a lower-layer liquid containing a viscous sediment. The upper- and lower-layer liquids were allowed to stand overnight at an ambient temperature, and the upper-layer liquid was separated to obtain a purified propolis-extract in the form of liquid having an absorbance ratio ($A_{310}/A_{660}$) of 8,322 and having a satisfactory color, flavor, taste and antiseptic activity in the yield of about 35% against the weight of the material solution containing a crude propolis-extract, d.s.b.

Similarly as the product in Example A-1, the product can be advantageously used intact as an antiseptic, antioxidant, anti-inflammatory agent and immunoactivator, and used in combination with other appropriate materials in food products, cosmetics and agents of anti-susceptive diseases.

EXAMPLE A-3

A massive propolis specimen was roughly grinded, added with 20-fold weights of 10 v/v % ethanol solution, and allowed to stand at 60° C. for 2 hours to effect extraction, followed by filtration. The filtrate (I) was removed and the sediment was extracted and washed similarly as above. The resultant sediment of propolis was added with 10-fold weights of 50 v/v % ethanol solution to effect extraction at 60° C. for 2 hours, followed by filtration. The filtrate (II) was recovered, and the resultant sediment was extracted with 50 v/v % ethanol solution and filtered similarly as above to obtain a filtrate (III). The filtrates (I), (II) and (III) were pooled, and the mixture was allowed to stand at 25° C. overnight and filtered to obtain a filtrate, a purified propolis-extract in the form of liquid having an absorbance ratio ($A_{310}/A_{660}$) of 4,840 and having a satisfiable color, flavor, taste and antiseptic activity in the yield of about 30% against the weight of the material propolis specimen, d.s.b.

Similarly as the product in Example A-1, the product can be advantageously used intact as an antiseptic, antioxidant, anti-inflammatory agent and immunoactivator, and used in combination with other appropriate materials in food products, cosmetics and agents of anti-susceptive diseases.

EXAMPLE A-4

An 80 v/v % aqueous ethanol solution containing a crude propolis-extract obtained by the method in Example A-1 was allowed to decrease the ethanol concentration to 45 v/v % in order to form upper- and lower-layer liquids in accordance with the method in Example A-1, and the resultant solution was allowed to stand at an ambient temperature for 5 hours, followed by separating the upper-layer liquid which was then diluted with equal amount of water and fed to a column packed with "Amberlite XAD-7", a synthetic macroporous resin commercialized by Rhom & Haas Company, Philadelphia, USA. The column was washed with water, and the effective components of propolis were eluted from the column with 95 v/v % aqueous ethanol solution to obtain a purified propolis-extract in the form of liquid having an absorbance ratio ($A_{310}/A_{660}$) of 30,415 and having a satisfiable color, flavor, taste and antiseptic activity in the yield of about 22% against the weight of the material solution containing a crude propolis-extract, d.s.b.

Similarly as the product in Example A-1, the product can be advantageously used intact as an antiseptic, antioxidant, anti-inflammatory agent and immunoactivator, and used in combination with other appropriate materials in food products, cosmetics and agents of anti-susceptive diseases.

EXAMPLE A-5

A crude propolis specimen was in an usual manner extracted with 85 v/v % aqueous methanol solution, and the resultant 80 v/v % aqueous methanol solution containing a crude propolis-extract (about 20 w/w %, d.s.b.) was added with water to decrease the methanol concentration to 45 v/v %, and allowed to stand at 50° C. for 30 min to form upper- and lower-layer liquids which were then allowed to stand overnight at an ambient temperature. The upper-layer liquid was separated, diluted with equal amount of water, and fed to a column packed with "HP-10", a synthetic macroporous resin commercialized by Mitsubishi Chemical Industries Ltd., Tokyo, Japan. The column was washed with water, and the effective components of propolis were eluted from the column with pure ethanol to obtain a purified propolis-extract in the form of liquid having an absorbance ratio ($A_{310}/A_{660}$) of 28,470 and having a satisfactory color, flavor, taste and antiseptic activity in the yield of about 20% against the weight of the material solution containing a crude propolis-extract, d.s.b.

Similarly as the product in Example A-1, the product can be advantageously used intact as an antiseptic, antioxidant, anti-inflammatory agent and immunoactivator, and used in combination with other appropriate materials in food products, cosmetics and agents of anti-susceptive diseases.

EXAMPLE A-6

A purified propolis-extract in the form of liquid prepared by the method in Example A-3 was diluted with an equal amount of water, and the resultant solution was fed to a column packed with "Amberlite XAD-7", a synthetic macroporous resin, washed with water, and fed with 95 v/v % aqueous ethanol solution to elute the effective components of propolis to obtain a purified propolis-extract in the form of liquid having an absorbance ratio ($A_{310}/A_{660}$) of 24,374 and having a satisfactory color, flavor, taste and antiseptic activity in the yield of about 25% against the weight of the material purified propolis-extract, d.s.b.

Similarly as the product in Example A-1, the product can be advantageously used intact as an antiseptic, antioxidant, anti-inflammatory agent and immunoactivator, and used in combination with other appropriate materials in food products, cosmetics and agents of anti-susceptive diseases.

EXAMPLE B-1

Gummy Candy

One hundred and fifty parts by weigh of "MABIT®", a hydrogenated maltose syrup commercialized by Hayashibara Co., Ltd., Okayama, Japan, was heated and concentrated in vacuo to give a moisture content of about 15 w/w %, and the resultant concentrate was in an usual manner mixed with a mixture which had been prepared by dissolving 13 parts by weight of gelatin in 18 parts by weight of water, one part by weight of a purified propolis-extract in the form of liquid prepared by the method in Example A-1, 2 parts by weight of citric acid, and adequate amounts of a flavor and color-imparting agent. The resultant mixture was formed and packed to obtain the captioned product.

The product is a gummy candy having a satisfactory texture and flavor, as well as being free of dental-carries inducibility.

EXAMPLE B-2

Chewing Gum

Three parts by weight of a gum base was melted by heating until it softened, and added with 4 parts by weight of sucrose and 3 parts by weight of maltose, and the mixture was added with a color-imparting agent and 0.02 parts by weight of a purified propolis-extract in the form of liquid prepared by the method in Example A-1, and the resultant mixture was kneaded with a roll, formed and packed to obtain the captioned product.

The product is a chewing gum having a satisfactory texture and flavor, and free of dental-carries inducibility because it contains the effective components of propolis.

EXAMPLE B-3

"Gyuhi" (Starch Paste)

To one part by weight of glutinous rice starch was added 1.2 parts by weight of water, and the mixture was heated to effect gelatinization while adding to the mixture 1.5 parts by weight of sucrose, 0.7 parts by weight of "SUNMALT®", a crystalline B-maltose powder commercialized by Hayashibara Co., Ltd., Okayama, Japan, 0.3 parts by weight of partial starch hydrolysate (thick malt syrup), and 0.02 parts by weight of a purified propolis-extract in the form of liquid prepared by the method in Example A-2. The resultant mixture was in an usual manner formed and packed to obtain the captioned product.

The product is a Japanese-style confectionery having a natural taste-enriched flavor and a satisfactory biting-property, as well as having an improved shelf-life and stability.

EXAMPLE B-4

Cream Filling

A mixture consisting of 1,200 parts by weight of "FINETOSE®", a crystalline α-maltose powder commercialized by Hayashibara Co., Ltd., Okayama, Japan, 1,000 parts by weight of shortening, 50 parts by weight of cacao mass, 3 parts by weight of a purified propolis-extract in the form of liquid prepared by the method in Example A-3, and one part by weight of lecithin, was in an usual manner kneaded to obtain the captioned product.

The product is a cream filling having a chocolate-like flavor and a satisfactory biting-property and meltability, and the quality and the shelf-life are stabilized and improved by the effective components of propolis.

EXAMPLE B-5

Lactic Acid Beverage

Ten parts by weight of defatted milk was sterilized by heating at 80° C. for 20 minutes, cooled to 40° C., added with 0.3 parts by weight of a starter, and fermented at about 37° C. for 10 hours. Thereafter, the mixture was homogenized, added with 5 parts by weight of an isomaltooligosaccharide syrup, one part by weight of sucrose and 2 parts by weight of an isomerized sugar syrup, and the resultant mixture was sterilized at 70° C., cooled and added with 0.2 parts by weight of a purified propolis-extract in the form of liquid prepared by the method in Example A-1, and bottled to obtain the captioned product.

The product is a high-quality lactic acid beverage having a satisfactory harmony of flavor and sweetness.

EXAMPLE B-6

Purified Propolis-extract Powder

Five parts by weight of a purified propolis-extract in the form of liquid prepared by the method in Example A-4 was admixed with 2 parts by weight of γ-cyclodextrin and 5 parts by weight of crystalline α-maltose, and the mixture was ventilated and dried at 40° C. for one hour, and mixed to homogeneity with 7 parts by weight of a crystalline α-maltose powder to obtain a purified propolis-extract powder. One g aliquots of the powder were distributed to laminated-aluminum bags and sealed.

The product has a satisfactory water-dispersibility and taste preference, and these render it advantageously useful as a health food, antiseptic, therapeutic agent, flavor-imparting agent, deodorant and agent for urine-therapy alone or in combination with other materials in order to maintain and promote health, as well as to prevent and treat diseases, and promote the recovery of health from diseases.

When the product is used as a health food, it can be directly administered to a recipient or administered by dissolving about 0.2–1 g of the product in 200 ml of tea, milk or juice, prior to use. When the product is used in urine-therapy, about 0.5–2 g of the product is dispersed or dissolved in 100 ml of fresh urine.

EXAMPLE B-7

Tablet

Ten parts by weight of L-ascorbic acid was added with 10 parts by weight of a purified propolis -extract powder prepared by the method in Example B-6, 19 parts by weight of a crystalline maltose powder, one part by weight of "αG rutin", an α-glycosyl rutin product commercialized by Toyo Sugar Refining Co., Ltd, Tokyo, Japan, were mixed to homogeneity and tabletted with a tabletting machine with a 20 R punch, diameter of 12 mm, to obtain a tablet.

The product is a readily swallowable mixed-vitamin-agent containing flavonoids derived from propolis, α-glycosyl rutin and L-ascorbic acid which is satisfactorily stabilized. The product can be advantageously used for the maintenance and promotion of health, the prevention and treatment of diseases, and the promotion of recovery of health from diseases.

EXAMPLE B-8

Therapeutic Ointment for Traumatic Injury

Five hundred parts by weight of a maltose powder was added with 20 parts by weight of an upper-layer liquid containing the effective components of propolis prepared by the method in Example A-5, and 33 parts by weight of methanol, and the mixture was added with 200 parts by weight of a 10 w/w % aqueous pullulan solution to obtain the captioned product having a satisfiable spreadability and adhesiveness.

The product exerts an antiseptic activity, anti-inflammatory activity and local anesthetic activity, as well as an energy-supplementing activity to a living cell exerted by maltose, and these activities shorten the cure time and satisfactorily heal a wounded part.

EXAMPLE B-9

Injection

A purified propolis-extract in the form of liquid prepared by the method in Example A-4 was dissolved in 30 v/v % aqueous ethanol solution, and the resultant solution was in an usual manner purified and filtered to obtain a pyrogen-free solution which was then distributed to 20 ml-glass vials to give a purified propolis-extract content of 5 mg, d.s.b. The vials were lyophilized and sealed to obtain the captioned product.

The product can be intramuscularly or intravenously administered to a recipient alone or in combination with other substances such as vitamins and minerals. The product can be advantageously used for the promotion of the treatment and the recovery of health during or after diseases such as immunopathies, circulatory diseases and nervous diseases.

EXAMPLE B-10

Injection

In 1,000 parts by weight of 2 v/v % aqueous ethanol solution were dissolved 6 parts by weight of sodium chloride, 0.3 parts by weight of potassium chloride, 0.2 parts by weight of calcium chloride, 3.1 parts by weight of sodium lactate, 45 parts by weight of maltose, and 0.1 part by weight of a purified propolis-extract in the form of liquid prepared by the method in Example A-4. The resultant mixture was in an usual manner purified and filtered to obtain a pyrogen-free solution, and 25 ml aliquots thereof were distributed to plastic containers to obtain the captioned product.

The product is an injection for supplementing energy and minerals, and can be advantageously used for the promotion of the treatment and the recovery of health during or after diseases.

EXAMPLE B-11

Intubation Nutrition

A composition consisting of 20 parts by weight of crystalline α-maltose, 1.1 parts by weight of glycine, 0.18 parts by weight of sodium glutamate, 1.2 parts by weight of sodium chloride, one part by weight of citric acid, 0.4 parts by weight of calcium lactate, 0.1 part by weight of magnesium carbonate, 0.1 part by weight of a purified propolis-extract prepared by the method in Example B-5, 0.01 part by weight of thiamine, and 0.01 part by weight of riboflavin was prepared. Twenty-four g aliquots of the composition were distributed to small laminated-aluminum-bags and heat-sealed to obtain the captioned product.

The product can be advantageously used as an orally or parenterally administrable intubation-nutrition which is administered by intubation feeding to the nasal cavity, stomach and intestine by dissolving one bag of the product in about 300–500 ml of water, prior to use.

EXAMPLE B-12

Bath Salts

A mixture consisting of 21 parts by weight of DL-sodium lactate, 8 parts by weight of sodium pyruvate, 5 parts by weight of a purified propolis-extract in the form of liquid prepared by the method in Example A-3, and 40 parts by weight of ethanol was mixed with 26 parts by weight of refined water and adequate amounts of a flavor and color-imparting agent to obtain the captioned product.

The product can be suitably used as a skin-refining agent and skin-whitening agent and used by diluting it 100–10,000-fold with hot water in a bathtub, when in use. The product advantageously used by diluting it similarly as above with a cleansing liquid or lotion, prior to use.

EXAMPLE B-13

Milky Lotion

A half part by weight of polyoxyethylene behenyl ether, one part by weight of polyoxyethylene sorbitol tetraoleate, one part by weight of oil-soluble glyceryl monostearate, 0.5 parts by weight of pyruvic acid, 0.5 parts by weight of behenyl alcohol, one part by weight of avocado oil, one part by weight of a purified propolis-extract in the form of liquid prepared by the method in Example A-2, and adequate amounts of an antiseptic and vitamin E were dissolved by heating in an usual manner, and the resultant solution was added with one part by weight of L-sodium lactate, 5 parts by weight of 1,3-butylene glycol, 0.1 part by weight of carboxy vinylpolymer and 85.3 parts by weight of refined water. The resultant mixture was emulsified by a homogenizer, added with an adequate amount of a flavor and mixed while stirring to obtain a milky lotion.

The product can be advantageously used as a sun-screening, skin-refining agent or skin-whitening agent.

EXAMPLE B-14

Cream

Two parts by weight of polyoxyethylene glycol monostearate, 5 parts by weight of self-emulsifying glycerine monostearate, 2 parts by weight of a purified propolis-extract in the form of liquid prepared by the method in Example A-6, one part by weight of liquid paraffin, 10 parts by weight of glyceryl trioctanate and an adequate amount of an antiseptic were dissolved by heating in an usual manner, and the resultant solution was added with 2 parts by weight of L-lactic acid, 5 parts by weight of 1,3-butylene glycol and 66 parts by weight of refined water. The resultant mixture was emulsified by a homogenizer, added with an adequate amount of a flavor and mixed while stirring to obtain a cream.

The product can be advantageously used as a sunscreening, skin-refining agent or skin-whitening agent.

Effect of the Invention

As described above, the process according to the present invention provides a purified propolis-extract, which contains the effective components of propolis in a readily absorbable- and utilizable-form in vivo, as well as having a relatively-high quality and a satisfactory flavor and taste, by effectively removing impurities, for example, resins, waxes and substances having a dark-brown color, a muddy smell and a stimulant taste, all of which are contained in conventional aqueous high-concentration solution containing a crude propolis-extract. Thus, the present purified propolis-extract can be used in a specific health-food, as well as in a wide variety of compositions such as food products, cosmetics and agents of anti-susceptive diseases.

The process according to the present invention is the most industrially realizable process, wherein a purified propolis-extract is separated and recovered as a fraction containing the effective components of propolis dissolved in a 30–55 v/v % solution of a readily water-soluble organic solvent.

While there has been described what is at present considered to be the preferred embodiments of the invention, it will be understood the various modifications may be made therein, and it is intended to cover in the appended claims all such modifications as fall within the true spirits and scope of the invention.

We claim:

1. A solution of propolis extract in a water soluble organic solvent, said propolis extract being substantially free of resins, waxes and dark colored impurities, said propolis extract obtained by the process comprising:

providing an aqueous solution of a water soluble organic solvent containing a crude propolis extract, wherein the concentration of said organic solvent in the aqueous solution is at least 70 v/v %;

decreasing the concentration of said organic solvent to a concentration in the range of 30–55 v/v %;

allowing the resultant solution to stand at ambient temperature for about 0.5–20 hours to form an upper layer containing components of propolis dissolved in said 30–55 v/v % solution of organic solvent and a lower layer containing sediments undissolved in said 30–55 v/v % solution of organic solvent; and separating and recovering said upper layer.

2. The propolis-extract solution of claim 1, wherein said water-soluble organic solvent is selected from the group consisting of methanol, ethanol, isopropanol, acetone and acetic acid.

3. A solution of propolis extract in a water soluble organic solvent, said propolis extract being substantially free of resins, waxes and dark colored impurities, said propolis extract obtained by the process comprising:

extracting a crude propolis specimen with an aqueous solution of a water soluble organic solvent to remove impurities, wherein the concentration of said organic solvent in the aqueous solution is less than 20 v/v %;

extracting the resultant sediment of propolis with an aqueous solution of said organic solvent having a concentration of 30–55 v/v % at ambient temperature for about 0.5–20 hours; and recovering the resultant extract.

4. The propolis-extract solution of claim 2, wherein said water-soluble organic solvent is selected from the group consisting of methanol, ethanol, isopropanol, acetone and acetic acid.

5. A composition comprising a therapeutically or prophylactically effective amount of a propolis extract according to claim 1 in a carrier selected from the group consisting of foods, beverages, cosmetically acceptable carriers, and pharmaceutically acceptable carriers.

6. The composition of claim 5, wherein the propolis-extract solution is present in an amount of about 1–25 w/w %.

7. A process for preparing a propolis-extract solution which is substantially free from resins, waxes, and dark colored impurities which comprises:

(a) providing a 30–55 v/v % aqueous solution of a water-soluble organic solvent having a therapeutically or prophylactically effective component of propolis;

(b) contacting the aqueous solution with a synthetic macroporous resin to absorb thereon said therapeutically or prophylactically effective component of propolis in the aqueous solution;

(c) eluting from the resin said therapeutically or prophylactically effective component of propolis absorbed therein; and (d) recovering the resultant therapeutically or prophylactically effective component of propolis.

8. The process of claim 7, wherein said water-soluble organic solvent is selected from the group consisting of methanol, ethanol, isopropanol, acetone and acetic acid.

9. The process according to claim 7, wherein step (a) further contains a step of diluting the aqueous solution with water to decrease the initial concentration of said organic solvent to a concentration of greater than about 20 v/v % but not higher than the initial concentration.

* * * * *